United States Patent
Propato

(10) Patent No.: US 7,778,710 B2
(45) Date of Patent: *Aug. 17, 2010

(54) METHOD AND APPARATUS FOR PREVENTING EXCESSIVE POWER DRAIN FROM AN IMPLANTABLE DEVICE

(75) Inventor: Claudio Propato, Saugus, CA (US)

(73) Assignee: Pacesetter, Inc., Sylmar, CA (US)

( * ) Notice: Subject to any disclaimer, the term of this patent is extended or adjusted under 35 U.S.C. 154(b) by 179 days.

This patent is subject to a terminal disclaimer.

(21) Appl. No.: 11/864,549

(22) Filed: Sep. 28, 2007

(65) Prior Publication Data

US 2008/0097532 A1 Apr. 24, 2008

Related U.S. Application Data

(63) Continuation of application No. 11/551,661, filed on Oct. 20, 2006, now Pat. No. 7,720,545.

(51) Int. Cl.
*A61N 1/372* (2006.01)
(52) U.S. Cl. .......................................... 607/59; 607/30
(58) Field of Classification Search .................. 607/30, 607/31, 59, 60
See application file for complete search history.

(56) References Cited

U.S. PATENT DOCUMENTS

| 4,197,850 | A | * | 4/1980 | Schulman et al. ............. 607/34 |
|---|---|---|---|---|
| 5,228,439 | A | * | 7/1993 | Mann et al. .................... 607/29 |
| 5,292,343 | A | | 3/1994 | Blanchette et al. |
| 6,007,493 | A | * | 12/1999 | Ericksen et al. ............. 600/508 |
| 7,270,633 | B1 | * | 9/2007 | Goscha et al. ............... 600/300 |
| 2002/0173702 | A1 | | 11/2002 | Lebel et al. |
| 2003/0028184 | A1 | | 2/2003 | Lebel et al. |
| 2003/0028284 | A1 | * | 2/2003 | Chirnomas .................. 700/231 |
| 2005/0131494 | A1 | | 6/2005 | Park et al. |
| 2005/0283198 | A1 | * | 12/2005 | Haubrich et al. ............... 607/30 |

OTHER PUBLICATIONS

U.S. Appl. No. 11/551,661, filed Oct. 2006, Propato.*
NonFinal Office Action (Restriction), mailed Mar. 6, 2009—Parent U.S. Appl. No. 11/551,661.
NonFinal Office Action, mailed Apr. 30, 2009—Parent U.S. Appl. No. 11/551,661.
NonFinal Office Action, mailed Nov. 13, 2009—Parent U.S. Appl. No. 11/551,661.
Final Office Action, mailed Feb. 1, 2010—Parent U.S. Appl. No. 11/551,661.
Notice of Allowance, mailed Mar. 22, 2010—Parent U.S. Appl. No. 11/551,661.

* cited by examiner

*Primary Examiner*—George R Evanisko
*Assistant Examiner*—Andrew Hayes

(57) ABSTRACT

A method and apparatus are provided for controlling interrogation of an implantable device such as a pacemaker, an implantable cardioverter, or a defibrillator utilizing an external device in a home environment. The method controls how frequently a patient can retrieve status information from the implantable device based on a time period elapsed since a last interrogation and a power level of a battery.

14 Claims, 5 Drawing Sheets

METHOD AND APPARATUS FOR PREVENTING EXCESSIVE POWER DRAIN FROM AN IMPLANTABLE DEVICE

CROSS-REFERENCE TO RELATED APPLICATIONS

This application is a continuation of U.S. patent application Ser. No. 11/551,661, filed Oct. 20, 2006, now U.S. Pat. No. 7,720,545 titled "Method and Apparatus for Preventing Excessive Power Drain from an Implantable Device".

FIELD OF THE INVENTION

Embodiments of the present invention pertain generally to implantable medical devices, such as cardiac pacemakers and implantable cardioverter defibrillators, and more particularly pertain to methods and apparatus that prevent excessive electrical power drain while exchanging information with devices outside the body.

BACKGROUND OF THE INVENTION

In the United States, it is estimated that approximately five million people have congestive heart failure ("CHF"). CHF is a life threatening condition that is managed by treating patients with drugs or implantable medical devices such as pacemakers and implantable cardioverter defibrillators ("ICD"). The information obtained through monitoring can be used to diagnose and treat a patient's condition.

Current ICDs and pacemakers have the ability to non-invasively communicate a patient's physical data and programmable parameters with a device such as an external programmer. The programmer is used to interrogate or program the ICD or pacemaker using a wireless, radio frequency telemetry link. Typically, a physician or medical professional utilizes the programmer, while the patient is in the medical office, to access data stored by the ICD or pacemaker, check and adjust on programmed parameters and the like. The programmer can also be used to instruct the ICD or pacemaker to execute desired functions, such as monitoring, stimulating, and storing diagnostic or other data. Conventional programmers in the marketplace allow numerous different parameters to be programmed. The ability to exchange data via a wireless link also permits the health care provider to reprogram or reconfigure the implantable device as required from time to time due to changes in the patient's condition. Recently, implantable devices have been proposed that allow a patient to operate certain types of home-based programmers to interrogate the implantable device in the privacy of the patient's own home. Heretofore, patients have been able to use the home-based programmers at any time to interrogate the implantable device.

However, home-based programmers present the opportunity for undue interrogation of the implantable device, and thus excessive drain on a battery of the implantable device. A power supply, typically a specialized battery, is housed within the implantable device to provide the electrical energy required for operation over an extended length of time. One difficulty is the efficient use of electrical energy. The lifetime of the battery depends on the power demands of the implantable device. For instance, implantable devices that require high speed and long range telemetry require greater battery power. ICDs also require a battery to operate at low current drains for long periods of time and simultaneously provide high current pulses. For example, the normal lifetime of a battery may be five years. To provide the longest battery life, it is desirable to reduce the power consumption required for the various functions of the implantable device. Because replacing a battery requires surgery, it is preferable that the battery last as long as possible.

Most implantable devices are configured to support interrogation by medically trained professionals in a medical office. Most implantable devices do not have the capability of allowing the patient to perform the interrogation at home, and therefore, there is not as great a concern with the drainage of battery power. However, as implantable devices are manufactured to include the feature of allowing a patient to interrogate the implantable device, additional power concerns emerge. Specifically, if a patient does not judiciously interrogate the device, for example if the patient checks the implantable device every few minutes, a heavy power drain on the battery will result. This, in turn, will affect the ability of the implantable device to communicate required patient data as well as affect the operation of the implantable device. Depletion of battery power will potentially lead to early failure of the implantable device and require the battery to be replaced more frequently.

A need remains for an improved implantable device including electrical circuitry and programmable features to limit the number of interrogations performed by a patient in a home environment in order to extend battery life.

SUMMARY

In accordance with one embodiment of the present invention, a method is provided for controlling interrogation of an implantable device. The method includes accepting, at the external device, a request for information from an implantable device after verifying a threshold period of time has elapsed since the last request for information.

In accordance with a further aspect of the invention, an external device, such as a programmer, requests information from an implantable device, which includes a monitoring module, a memory module, and an input/output ("I/O") module having a telemetry unit. The monitoring module records the last request for information from the patient's external device to the memory module and verifies a threshold period of time has elapsed since the last request for information. The telemetry unit establishes a wireless communication link with the external device and transmits the requested information stored within the memory module based on the amount of time elapsed since the last request for information.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

In the following detailed description, reference is made to the accompanying drawings which form a part hereof, and in which is shown by way of illustration specific embodiments in which the present invention may be practiced. These embodiments, which are also referred to herein as "examples," are described in sufficient detail to enable those skilled in the art to practice the invention, and it is to be understood that the various embodiments of the invention may be combined, or that other embodiments may be utilized and that structural, logical and electrical changes may be made without departing from the scope of the present invention. For example, embodiments may be used with a pacemaker, a cardioverter, a defibrillator, and the like. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated.

Figure 1:
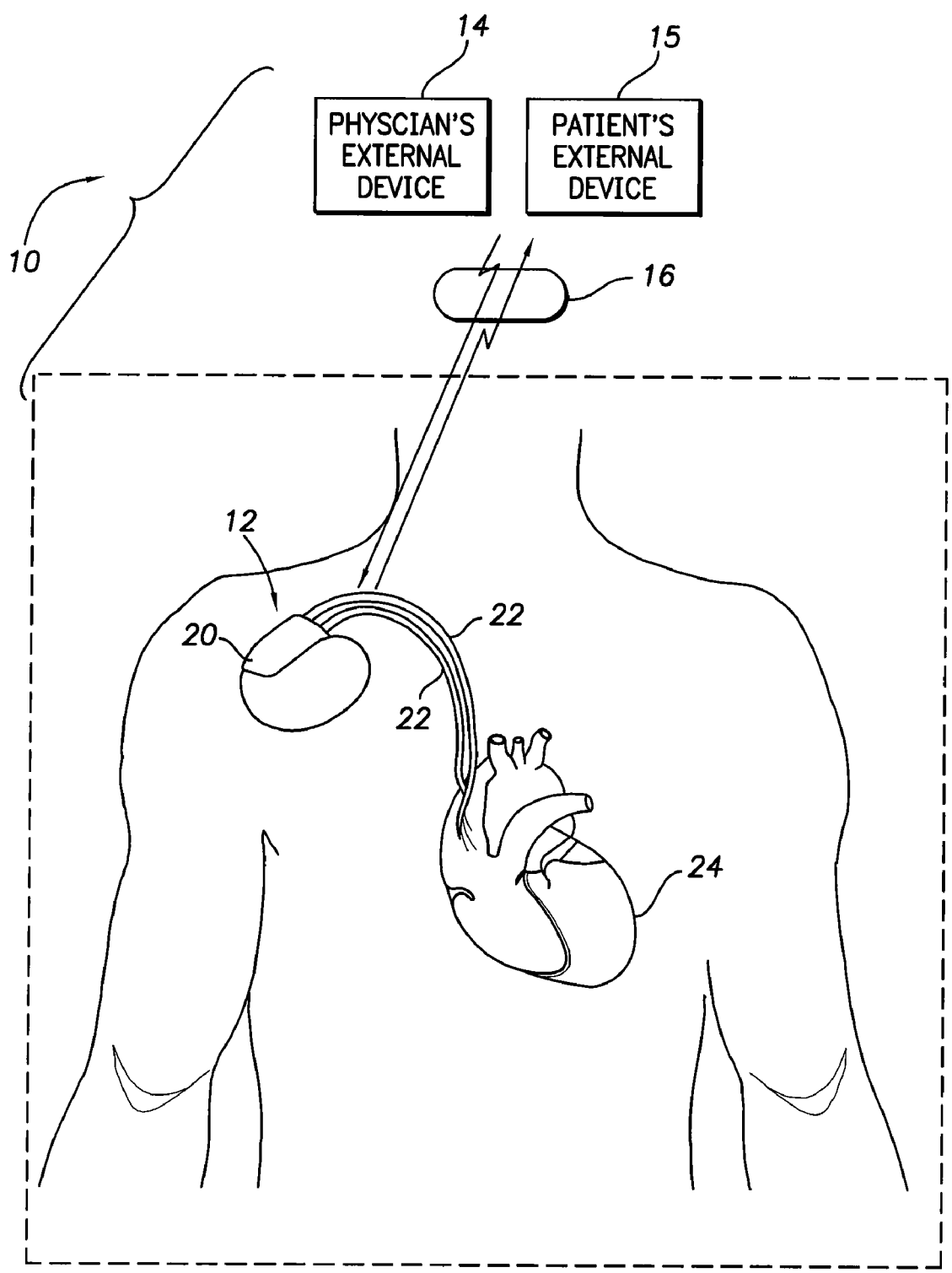
FIG. 1 illustrates an implantable device formed in accordance with one embodiment of the present invention that remotely communicates with an external programmer.

FIG. 1 illustrates a programmable cardiac system 10 that includes an implantable device 12 in communication with a clinician's external device 14 and a patient's external device 15 via a communication link 16 that is controlled in accordance with an embodiment of the present invention. The implantable device 12 includes a connector 20 that is joined to a plurality of leads 22. Physiological information is detected over the leads 22 that are located with or near a heart 24 at either an atrium, a ventricle or both. The physiological information is provided through leads 22 via connector 20 to the implantable device 12. The implantable device 12 monitors the heart 24 of a patient and detects when the patient is having a post-myocardial infarct, a "silent" myocardial infarct, a myocardial infarct, an ischemia, a heart block, an arrhythmia, a fibrillation, or a congestive heart failure.

Additionally, the implantable device 12 provides an electrical stimulation through the leads 22 based on the physiological information detected. For example, stimulation may be provided when the intrinsic heartbeat is insufficient, when depolarization is not being conducted through the heart 24, when the heart rate is too slow to maintain adequate blood from to the body and the like. In addition, implantable device 12 detects electrical characteristics of heart 24 subject to a preventative pacing scheme such as bi-ventricular, right ventricular, left ventricular, left atrial, right atrial, and bi-atrial pacing. By monitoring the excitability of cardiac tissue and its response to different pacing schemes, the implantable device 12 is able to provide a physician with information as to the patient's physiological condition, e.g., whether it has improved or is progressing towards cardiac failure.

A physician can utilize the external device 14 to access information stored within the implanted device 12. The external device 14 may be implemented as a programmer in accordance with an embodiment of the present invention. Information is accessed from the implantable device 12 after the communication link 16 is established between the implantable device 12 and the external device 14.

The external device 14 permits a physician to examine the operation of the implantable device 12. During an office visit, the physician has the ability to review physiological data and programmed parameters of the implantable device 12, as well as to adjust these parameters through the external device 14 depending on the physiological condition of the patient. Some parameters that a physician may be interested in programming include fibrillation detection rate, tachycardia detection rate, ventricular fibrillation detection rate, ventricular tachycardia detection rate, and the like. Setting a defibrillation detection rate too low may result in an unnecessary defibrillation that is both painful and potentially damaging to the heart. On the other hand, setting a detection rate too high may cause the required electrical shock not to be applied in a timely manner to a fibrillating heart and the patient may die.

In home-based applications, the patient is limited to certain functions that he/she can access through the external device 15 while at home. Thus, the patient should be allowed to access a restricted set of information, such as the patient's overall cardiac physiological condition, whether to consult a physician or not, and the status of the implantable device, e.g., battery power condition.

Figure 2:
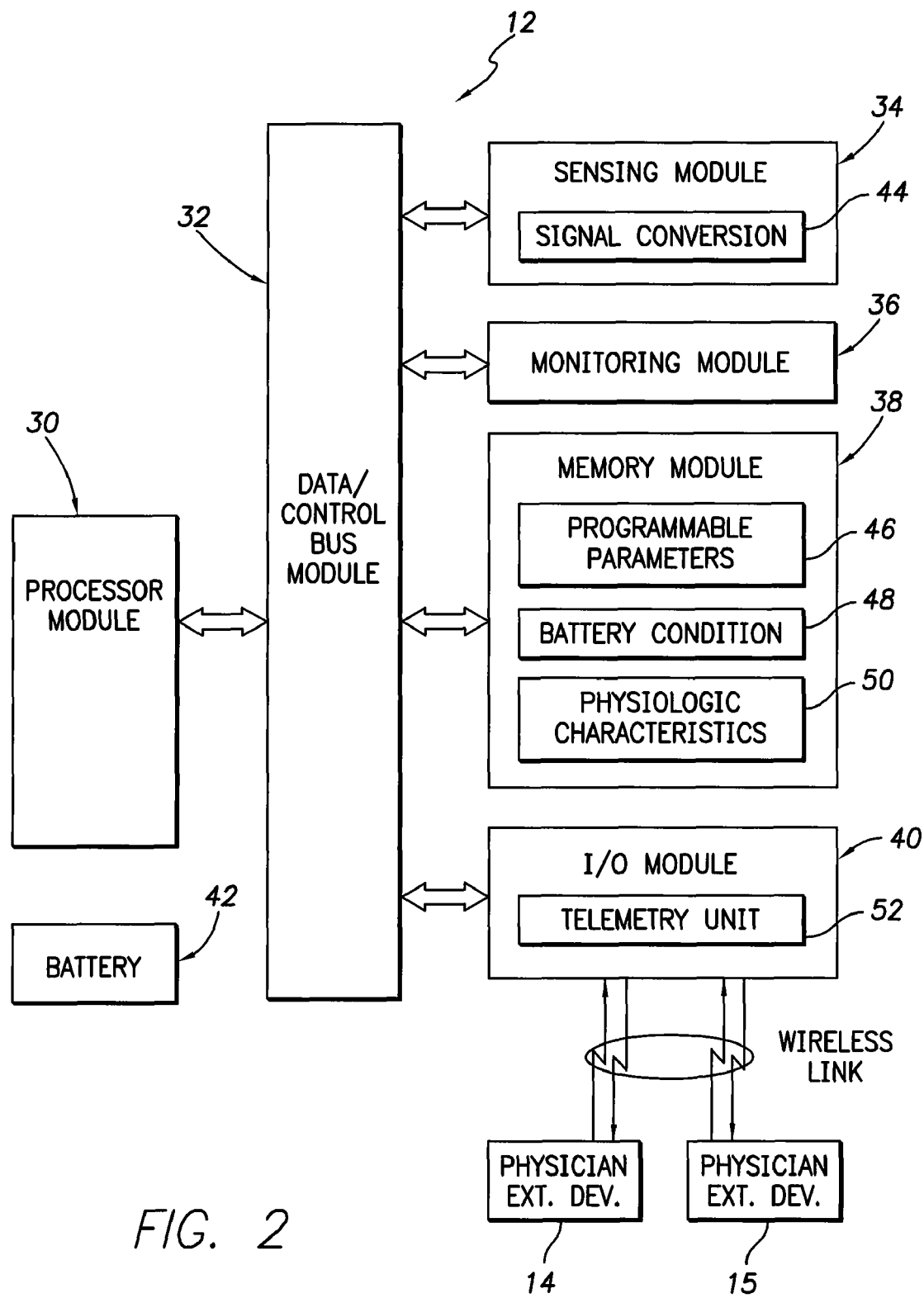
FIG. 2 illustrates a block diagram of an implantable device in communication with an external programmer utilized in accordance with an embodiment of the present invention.

FIG. 2 illustrates a block diagram of a portion of implantable device 12. The implantable device 12 may be a cardiac pacemaker, an implantable cardioverter defibrillator ("ICD"), a defibrillator, or an ICD coupled with a pacemaker implemented in accordance with an embodiment of the present invention. The implantable device 12 includes a processor module 30, a data/control bus module 32, a sensing module 34, a monitoring module 36, a memory module 38, an Input/Output ("I/O") module 40, and a battery 42. It is understood that data/control bus module 32, sensing module 34, monitoring module 36 and I/O module 40 are conceptual blocks, not necessarily separate hardware and may be implemented in software by the processor module 30.

Processor module 30 typically includes a microprocessor, a microcomputer, or equivalent control circuitry for processing physiological characteristics of the heart 24. The processor module 30 may further include RAM or ROM memory, logic and timing circuitry, state machine circuitry, and I/O circuitry. Typically, the processor module 30 includes the ability to process or monitor data as controlled by a program code stored in a designated block of memory. Data/control bus module 32 represents a hardware or software interface between the various functional modules of the implantable device 12.

Sensing module 34 includes a signal conversion module 44. The sensing module 34 receives physiology signals from the leads 22, such as a depolarization wave as it spreads through the cardiac tissue and measures the timing, direction of propagation, and point of initiation of successive depolarization waves. The depolarization may be a result of an inherent cardiac cycle or in response to a cardiac pacing event, such as pacing the heart utilizing bi-ventricular pacing, right ventricular pacing, left ventricular pacing, left atrial pacing, right atrial pacing or bi-atrial pacing. The signal conversion module 44 typically includes an analog-to-digital ("A/D") converter (not shown) and receives raw analog signals that are voltages that result from the change in ionic concentrations of sodium and calcium through the cardiac tissue that occur during depolarization. The signal conversion module 44 converts the raw analog signals to a plurality of digital signals. The digital signals are transferred over the data/control bus module 32 and stored in the memory module 38.

The monitoring module 36 analyzes the digital physiology signals from the signal conversion module 44 and identifies desired physiologic characteristics. For example, the monitoring module 36 may identify arrhythmias, trends in cardiac behavior, and the like. The monitoring module 36 determines the programmed state of the implantable device 12 and determines the remaining battery power, which is stored as battery condition 48. As previously mentioned the implantable device 12 can be programmed by a physician to operate in a specific mode, e.g., detect ventricular fibrillation and deliver an associated therapy. The monitoring module 36 verifies and records that the implantable device 12 is in the correct programmed state (e.g., not a harmful state) and the amount of time within each state. If the monitoring module 36 detects a harmful state, it will report a warning to the external device 14 or to the patient's external device 15 through the I/O module 40. The monitoring module 36 also collects timing information that includes a time the data is transmitted, a date the data is transmitted, a number of total interrogations performed, and the date and time of each interrogation request. The monitoring module 36 also monitors operation of the implantable device 12 in connection with receipt and transmission of information and parameters by and from the telemetry unit 52.

In addition, each time a request to interrogate the implantable device 12 is made by the external device 15, the monitoring module 36 checks on the status of the battery 42 and records the battery condition 48 in the memory module 38. As the power of the battery decreases, the monitoring module 36 extends the time period required to accept a new interrogation. If the battery power is below a threshold level, the monitoring module 36 will prevent further responses to patient's external device 15. The battery power level depends on the type and size of battery 42 utilized by the implantable device 12. Typical batteries 42 include zinc-mercury batteries, nickel-cadmium batteries, nuclear batteries, fuel cells, lithium iodine batteries and the like. The monitoring module 36 also checks on the frequency of interrogations. If a specified threshold time period has not lapsed when an interrogation is requested, the monitoring module 36 prevents the interrogation from being answered.

The memory module 38 includes blocks of memory allocated to store programmable parameters 46, a communications log 47, a battery condition 48, and physiological characteristics 50. The blocks of memory may be ROM, PROM, EPROM, EEPROM, RAM, SRAM, DRAM, DDRAM, EDO, SDRAM, Flash, MRAM, FRAM, EEPROM, EAPROM and the like. The communications log 47 records data related to past communications to and from the implantable device 12. For example, the communications log 47 may include a time at which each incoming transmission is received, a time at which each outgoing transmission was transmitted, a length of each outgoing transmission, a nature or type associated with incoming and outgoing transmissions and an identification of the implantable device 12, as well as an identification of the type of device requesting information, e.g., the physician's external device 14 or the patient's external device 15. The nature or type of the transmission and length thereof may be of interest to estimate an amount of battery power used in connection with the transmission by the implantable device 12.

The programmable parameters 46 may include a tachycardia detection rate, a fibrillation detection rate, a ventricular tachycardia rate, a ventricular fibrillation detection rate, a bradycardia rate, stability algorithm settings, onset algorithm settings, specific therapies for each cardiac zone, a duration of therapy required for each cardiac zone and the like. The battery condition 48 may include a low power battery status, a battery internal resistance, a number of charge/discharge cycles, battery age, and a remaining battery charge. The physiological characteristics 50 may include a series of digitized data signals detected by the leads 22 over time and/or a patient's heart rate, an electrical activation pattern of the heart, a strength of contraction of heart muscle, and an amount of fluid in the lungs. Furthermore, the physiological characteristics 50 may also include a possible current condition of the patient, such as a patient's tachycardia rate, a patient's bradycardia rate, a patient's fibrillation rate, and a patient's arrhythmia rate or whether the patient is suffering from a myocardial infarction, a post-myocardial infarction, a "silent" myocardial infarction, an ischemia, an arrhythmia, a heart block, a fibrillation, or a congestive heart failure. These physiological characteristics 50 may be transmitted as physiologic information by a telemetry unit 52 to the physician's external devices 14 or to the patient's external device 15.

Input/Output ("I/O") module 40 includes a telemetry unit 52. The telemetry unit 52 enables the implantable device 12 to download data to the physician's external device 14 when a patient is at the physician's office or to the patient's external device 15 when the patient is at home via a wireless link 16. The telemetry unit 52 interfaces with processor module 30 and monitoring module 36 to determine whether to perform an interrogation. A patient that does not exercise discretion when making requests for interrogation via the external device 15 can wear down the battery 42. A low battery condition may be defined as at least 10% of the maximum battery power level, or as a power level that leads to imminent battery power failure. The lifetime of the battery 42 depends on the power demands of the implantable device 12 as well as the frequency of interrogations. For instance, the implantable device 12 may require the battery 42 to operate at low current drains for long periods of time and simultaneously provide high current pulses. To provide the longest battery life, it is desirable to reduce the power consumption required for the various functions of the implantable device 12. By limiting a patient's ability to interrogate the implantable device 12, battery power is conserved.

Figure 3:
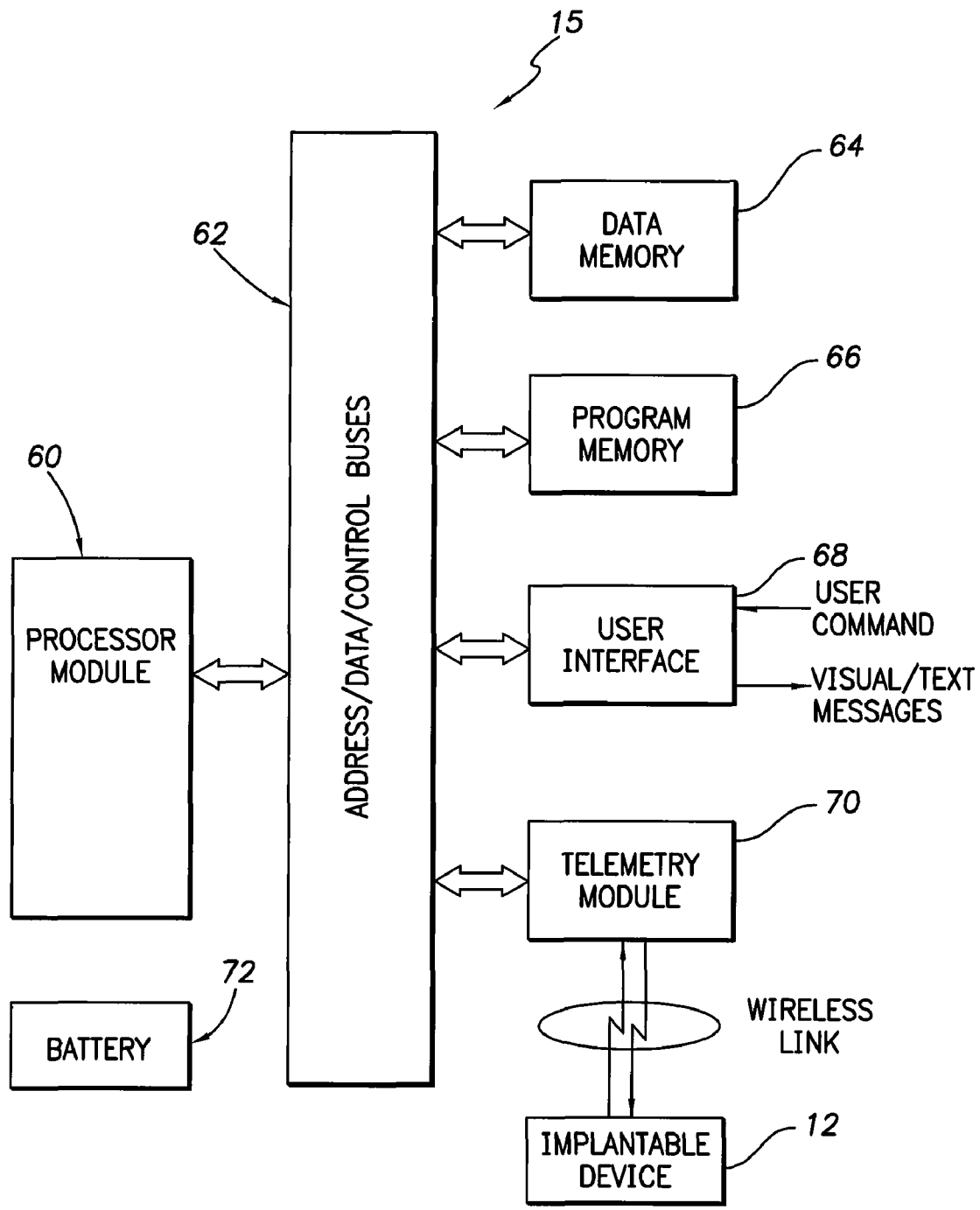
FIG. 3 illustrates a block diagram of an external device in communication with an implantable device, as shown in FIG. 2, utilized in accordance with an embodiment of the present invention.

FIG. 3 illustrates a block diagram of a patient's external device 15 in accordance with an embodiment of this invention. The patient's external device 15 includes a processor module 60, an address/data/control bus module 62, a data/memory module 64, a program memory module 66, a user interface module 68, a telemetry module 70 and a battery 72. Address/data/control bus module 62, data/memory module 64, program memory module 66, user interface module 68 and telemetry module 70 represent hardware blocks that may partially or totally implemented on the same semiconductor die.

Processor module 60 typically includes a microprocessor, a microcomputer, or equivalent control circuitry for processing a request to interrogate an implantable medical device 12. The processor module 60 may further include RAM or ROM memory, logic and timing circuitry, state machine circuitry, and I/O circuitry. Typically, the processor module 60 includes the ability to process or monitor data as controlled by a program code stored in program module 66.

Address/data/control bus module 62 represents a hardware interface between the various functional modules of the patient's external device 15.

The data memory module 64 includes blocks of memory allocated to store physiological information, timing information that includes a time the data is transmitted, a date the data is transmitted, a number of total interrogations performed, and the date and time of each interrogation request, and a battery condition.

The program memory module 66 includes blocks of memory allocated to store a program code that instructs processor 60 regarding the operation of external device 15. For instance, the program code may include instructions on how the user may interface with the external device 15, what information the user may be allowed to access, and what format messages will be provided to the user (e.g., visual, textual, auditory).

The blocks of memory may be ROM, PROM, EPROM, EEPROM, RAM, SRAM, DRAM, DDRAM, EDO, SDRAM, Flash, MRAM, FRAM, EEPROM, EAPROM and the like.

The user interface 68 accepts commands from the user and displays the requested interrogation information, and the telemetry module 70 interfaces with the implantable device 12 over a wireless link. Further, the telemetry unit 70 is commanded by processor module 60 to communicate with the implantable device 12. Patient's external device 15 also includes a battery 72.

In one embodiment of the present invention, the processor module 60 monitors each time a request is made by the user utilizing external device 15 to interrogate the implantable medical device 12. The processing module 60 checks data memory 64 for the last time the user made a request. If a specified threshold time period has not lapsed when an interrogation is requested, the processor module 60 prevents the interrogation from being performed. If the specified threshold time period has lapsed, the processor 60 performs an interrogation of implantable device 15 via telemetry module 70. The processor module 60 monitors the receipt and transmission of information and parameters by and from the telemetry unit 70 to ensure communication is successful. The processor module 60 then logs the interrogation in data memory 64. For example, the processor 60 may, for example, log a time at which each incoming transmission is received, a time at which each outgoing transmission was transmitted, a length of each outgoing transmission, a nature or type associated with incoming and outgoing transmissions and an identification of the implantable device 12. The processor 60 utilizes user interface 68 to show/display the requested information to the user.

Figure 4:
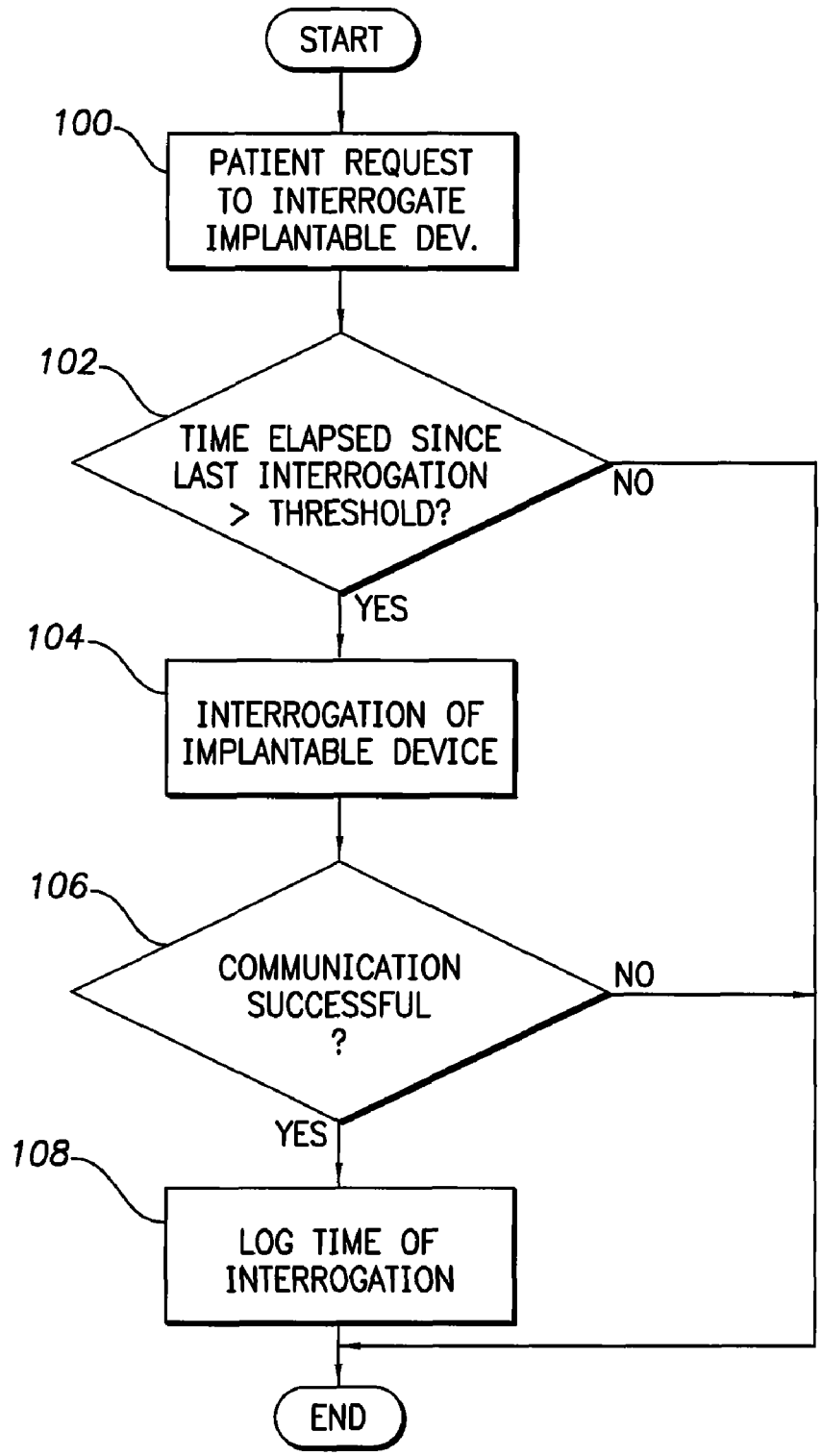
FIG. 4 illustrates a flow chart for a process to control interrogation of an implantable device based on the time lapse since the last interrogation stored in the patient's external device in accordance with an embodiment of the present invention.

FIG. 4 illustrates a process to control the interrogation of the implantable device 12 utilizing the patient's external device 15 in accordance with at least one embodiment of the present invention. At 100, the patient utilizes the external device 15 to make a request to interrogate the implantable medical device 12. At 102, the external device 15 compares the time elapsed from the last request for interrogation with a value for the current time threshold. The time threshold is the amount of time that must elapse before an interrogation is permitted. If the time elapsed from the last interrogation is less than the required time threshold, external device 15 denies the request and no interrogation to implantable device 12 is initiated. The patient must wait until the time threshold has elapsed before making another request for interrogation.

The time threshold is dynamically modified by the device that keeps record of the time elapsed since last interrogation (e.g., either patient's external device 15 or implantable device 12) based on the battery power level reported by implantable device 12. Table 1 shows an embodiment of how the time threshold can be modified based on implantable device 12's battery power level.

TABLE 1

| BATTERY POWER STATUS | TIME THRESHOLD |
| --- | --- |
| FULL | Thr1 |
| MID | Thr2 > Thr1 |
| LOW | Thr3 > Thr2 |
| CRITICAL | Thr4 > Thr3 |

For instance, when the battery power level is "full" (e.g. battery is fully charged) the time threshold is initially at a value of Thr1. In one embodiment, Thr1 may allow the patient to perform an interrogation utilizing the patient's external device 15 once per hour. In another embodiment, Thr1 may allow the patient to perform an interrogation once per day. As the battery power decreases to a "mid" level (e.g. 50% power charge), processor module 30 will assign a new time threshold value, Thr2, where Thr2 will have a greater value than Thr1. Thus, Thr2 will restrict the frequency of interrogation in comparison to Thr1. In one embodiment, Thr2 may allow the patient to perform an interrogation utilizing the patient's external device 15 up to once a week. In another embodiment, Thr2 may allow an interrogation to be performed once a month. As the battery power level decreases to a "low" level (e.g. less than 50%), processor module 30 will assign Thr3 as the time threshold value. The value or Thr3 will be greater than Thr2. In one embodiment, Thr3 may allow a patient to interrogate the implantable medical device 12 once every three months. In an alternative embodiment, Thr3 may allow a patient to perform an interrogation once every six months. As the battery power level drops to a "critical" level (e.g. less than 10%), process module 30 will assign Thr4 as the time threshold value. At the "critical" level, the maximum time period allowable is assigned to a time threshold value. In one embodiment, Thr4 will not allow the patient to perform any interrogations of implantable device 12. There can be a plurality of time thresholds. For example, in one embodiment, a time threshold can be assigned for every 10% drop in battery power (e.g., 100% corresponds to Thr1, 90% corresponds to Thr2, 80% corresponds to Thr3, 70% corresponds to Thr4, etc., and at the "critical" level 10% corresponds to Thr10).

If the time elapsed from last interrogation is longer than the required time threshold per 102, then at 104, patient's external device 15 sends a request for interrogation via a wireless connection to implantable device 12. Telemetry unit 52 receives the request for interrogation, and transfers the request via data bus 32 to monitoring module 36. The Process module 30 then retrieves the required information from the memory module 38 and has the I/O module 40 transfer the requested information to the patient's external device 15.

At 106, I/O module 40 monitors the process of interrogation and the status of the wireless connection. If the wireless connection fails or the communication between the external device 15 and the implantable medical device 12 fails for any reason during the interrogation process, monitoring module 36 will end the process. No log will be kept of the interrogation, and the patient must request another interrogation.

At 106, if the interrogation proceeds successfully, then at 108 a log of the interrogation (e.g. time and date of interrogation) will be made and stored on patient's external device 15.

Figure 5:
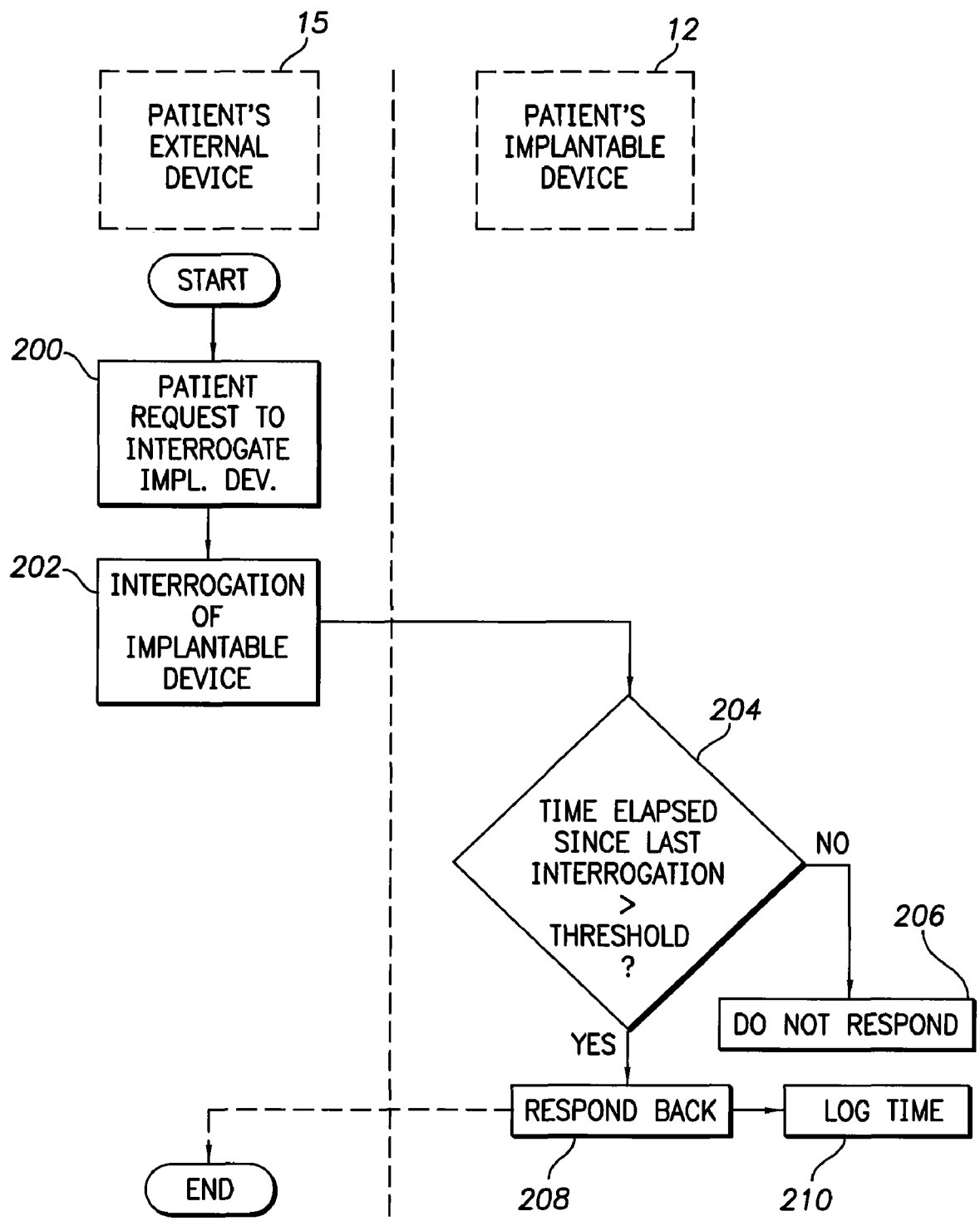
FIG. 5 illustrates a flow chart for a process to control interrogation of an implantable device based on the time lapse since the last interrogation stored in the implantable device in accordance with an embodiment of the present invention.

FIG. 5 illustrates a processing sequence where the time logs of an interrogation are stored in the implantable device 12 in accordance with an embodiment of this invention. Beginning at 200, the patient controls external device 15 and starts a request to interrogate the implantable device 12. For example, in one embodiment, the patient may push a button on external device 15 to request an interrogation.

At 202, the patient's external device 15 initiates the interrogation by sending a request via a wireless connection to the implantable device 12. In one embodiment, external device 15 may be inductively coupled with the implantable device 12. The request is received by telemetry unit 52 and the request is transferred along data bus 32 to monitoring module 36.

At 204, processor module 30 checks if the time elapsed from the last interrogation from external device 15 is longer than the current time threshold value. If the threshold has not expired, the process will be terminated at 206 and no response will be made. However, if the threshold value has expired, the process continues. At 208, implantable device 12 responds to external device 15 by having processor 30 retrieve the requested information from memory module 38 and transmit the information via I/O module 40 to external device 15. At 210, implantable device 12 logs the time and date of the interrogation in memory module 38.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

What is claimed is:

1. A system for controlling interrogation of an implantable device utilizing an external device, the system comprising:
    said implantable device;
    a module, in the implantable device, adapted to receive a current request for information to be retrieved from the implantable device;
    a monitoring module, in the implantable device, adapted to record a temporal history of previous interrogations of the implantable device, to compare the temporal history of previous interrogations with the current request for information, and to decide whether to allow the interrogation process to proceed based on the comparison; and
    a telemetry unit adapted to establish a wireless communication link with the external device;
    wherein the monitoring module is adapted to prevent the interrogation process from proceeding when a period of time elapsed since a last request for the information is shorter than a threshold period of time.

2. The system according to claim 1, wherein the information requested includes at least one of physiological information, programmable information, timing information, and a battery condition.

3. The system according to claim 1, wherein the information constitutes physiological information that includes at least one of a heart rate, an electrical activation pattern of the heart, a strength of contraction of heart muscle, an amount of fluid in the lungs, a tachycardia rate, a bradycardia rate, a fibrillation rate, and an arrhythmia rate.

4. The system according to claim 1, wherein the information constitutes battery condition that includes at least one of a low power battery status, a battery internal resistance, a number of charge/discharge cycles, battery age, a battery voltage and a remaining battery charge.

5. The system according to claim 1, wherein the monitoring module is adapted to prevent the implantable device from proceeding with the interrogation process when a battery power level is below a threshold battery value.

6. The system according to claim 1, wherein the implantable device constitutes at least one of a pacemaker, an implantable cardioverter defibrillator, and a defibrillator.

7. A system controlling interrogation of an implantable device utilizing an external device, the system comprising:
    said implantable device;
    a module, in the implantable device, adapted to receive a current request for information to be retrieved from the implantable device;
    a monitoring module, in the implantable device, adapted to record a temporal history of previous interrogations of the implantable device, to compare the temporal history of previous interrogations with the current request for information, and to decide whether to allow the interrogation process to proceed based on the comparison; and
    a telemetry unit adapted to establish a wireless communication link with the external device;
    wherein the monitoring module, in the implantable device, is further adapted to check the battery condition including the power level of the battery; and
    wherein the monitoring module, in the implantable device, dynamically updates the threshold period of time to a new value based on said power level of a battery within the implantable device, the threshold period of time used in comparison of the temporal history of previous interrogations with the current request for information.

8. A method for controlling interrogation of an implantable device utilizing an external device, the method comprising:
    receiving a current request for information, at the implantable device, to be retrieved from an implantable device;
    determining, by the implantable device, a temporal history of previous interrogations of the implantable device;
    comparing, by the implantable device, the temporal history of previous interrogations with the current request for information and with a threshold period of time that is to elapse before accepting a new request for information;
    allowing the interrogation process to proceed based on the comparing;
    transmitting information from the implantable device to the external device;
    checking and recording a battery condition; and
    as the battery condition decreases, extending, at the implantable device, the threshold period of time that is to elapse before accepting a new request for information.

9. The method according to claim 8, wherein the transmitting information includes reading the information from a memory location within the implantable device.

10. The method according to claim 8, wherein the information includes at least one of physiological information, programmable information, and timing information.

11. The method according to claim 8, wherein the battery condition comprises a battery power level and wherein the method further comprises preventing, by the implantable device, transmission of the information when the battery power level is less than a threshold battery value.

12. The method according to claim 8, wherein the implantable device constitutes at least one of a pacemaker, an implantable cardioverter defibrillator, and a defibrillator.

13. The method according to claim 8, further comprising storing, in memory of the implantable device, at least one of a time and date of when data is transmitted from the implantable device, a number of total interrogations performed, and a time and date of each interrogation.

14. The method according to claim 8, wherein the determining operation is performed by a monitoring module in the implantable device after receiving a request for information from the external device.

* * * * *